(12) United States Patent
Greenberg et al.

(10) Patent No.: US 6,751,498 B1
(45) Date of Patent: *Jun. 15, 2004

(54) APPARATUS AND METHOD FOR NON-INVASIVE, PASSIVE FETAL HEART MONITORING

(75) Inventors: Robert S. Greenberg, Glenelg, MD (US); John A. Christion, Columbia, MD (US); Edward J. Moses, Rockville, MD (US); Wayne I. Sternberger, Highland, MD (US)

(73) Assignee: The Johns Hopkins University, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/522,664

(22) Filed: Mar. 10, 2000

Related U.S. Application Data
(60) Provisional application No. 60/124,447, filed on Mar. 15, 1999.

(51) Int. Cl.$^7$ .................................................. A61B 5/04
(52) U.S. Cl. ....................................................... 600/511
(58) Field of Search ........................................ 600/511

(56) References Cited

U.S. PATENT DOCUMENTS

| | | | |
|---|---|---|---|
| 4,256,118 A | 3/1981 | Nagel | 128/733 |
| 4,519,396 A | * 5/1985 | Epstein et al. | |
| 4,569,356 A | 2/1986 | Kyozuka | 128/698 |
| 4,573,479 A | 3/1986 | Tuccillo | 128/698 |
| 4,781,200 A | 11/1988 | Baker | 128/670 |

(List continued on next page.)

OTHER PUBLICATIONS

J. Karin, M. Hirsch, O. Segal, S. Akselrod; Non Invasive Fetal ECG Monitoring; pp. 365–368; Computers in Cardiology 1994; 1994 IEEE.

Victor Mor–Avi, Yael Amitay, Allan Jorge, Claudia Korcarz, Joanne Sandelski, Jakob Karin, Roberto M. Lang, Solange Akselrod; Spectral Analysis of Beat–to–Beat Fluctuations in Left Ventricular Area Signals Obtained Using Acoustic Quantification; pp. 99–102; Computers in Cardiology 1995; 1995 IEEE.

S. Akselrod, J. Karin, M. Hirsch; Computerized Detection of Fetal ECG From Maternal Abdominal Signal; pp. 261–264; School of Physics and Astronomy, Tel–Aviv–University; Belinson Medical Center, Petah–Tikva, Israel IEEE Comp in Cardiol 1987.

*Primary Examiner*—Mark Bockelman
(74) *Attorney, Agent, or Firm*—Francis A. Cooch

(57) ABSTRACT

An apparatus and method for fetal heart and maternal heart and uterine monitoring is provided which acquire biopotential waveforms indicative of the mother's heart beat from sensors located at or near the mother's chest, and waveforms indicative of the combined maternal and fetal heart beats from abdominal sensors located on the mother's abdomen, lower back, or both. The signals from the abdominal sensors are divided into a plurality of channels. An adaptive signal processing filter (ASPF) algorithm or other suitable algorithm is then used to cancel the estimated maternal waveform from each channel derived from the abdominal sensors. The system then selects from the resulting waveforms at least one waveform to serve as the reference fetal waveform. The reference waveform is then processed against the other abdominal waveforms preferably using the ASPF algorithm again to form an enhanced fetal signal that is a representation of the fetus's biopotential electrocardiogram ($EKG_f$). The $EKG_f$ can subsequently be used to measure fetal heart rate and other biophysical profile parameters. Surface electromyogram (EMG) signals allow for concurrent monitoring of uterine contractions and afford improved cancellation of motion artifacts.

3 Claims, 8 Drawing Sheets

U.S. PATENT DOCUMENTS

| | | | |
|---|---|---|---|
| 4,898,179 A | 2/1990 | Sirota .......................... | 128/670 |
| 4,945,917 A | 8/1990 | Akselrod et al. ........... | 128/696 |
| 5,025,787 A | 6/1991 | Sutherland et al. ......... | 128/642 |
| 5,025,795 A | 6/1991 | Kunig ........................ | 128/713 |
| 5,042,499 A | 8/1991 | Frank et al. ................. | 128/698 |
| 5,123,420 A | 6/1992 | Paret .......................... | 128/698 |
| 5,170,791 A | 12/1992 | Boos et al. ............ | 128/661.07 |
| 5,184,619 A | 2/1993 | Austin ........................ | 128/639 |
| 5,209,237 A | 5/1993 | Rosenthal ................... | 128/698 |
| 5,257,627 A | 11/1993 | Rapoport ............... | 128/661.07 |
| 5,372,139 A | 12/1994 | Holls et al. .................. | 128/698 |
| 5,373,843 A | 12/1994 | Quedens et al. ............ | 128/642 |
| 5,509,416 A | 4/1996 | Wilmott ................ | 128/661.07 |
| 5,524,631 A | 6/1996 | Zahorian et al. ............ | 128/698 |
| 5,529,064 A | 6/1996 | Rall et al. ................... | 128/633 |
| 5,546,953 A | 8/1996 | Garfield ....................... | 128/733 |
| 5,596,993 A | 1/1997 | Oriol et al. ................. | 128/698 |
| 5,807,271 A * | 9/1998 | Tayebi et al. ............... | 600/511 |
| 5,833,622 A * | 11/1998 | Meathrel et al. | |

* cited by examiner

APPARATUS AND METHOD FOR NON-INVASIVE, PASSIVE FETAL HEART MONITORING

The present application claims the benefit of earlier filed U.S. Provisional Application No. 60/124,447, filed Mar. 15, 1999, which is incorporated herein in its entirety by reference.

BACKGROUND OF THE INVENTION

1. Field of Invention

The invention relates generally to biomedical devices and, in particular, comprises a non-invasive and passive apparatus and method that uses sensors and signal processing techniques to monitor fetal electrocardiographic waveform ($EKG_f$), heart rate, heart rate variability and heart vector orientation and maternal heart rate and uterine contraction noise artifacts.

2. Description of the Related Art

Though the perinatal mortality rate in the United States has decreased significantly in the past three decades, the vast majority of the current perinatal deaths are thought to be attributable to potentially preventable etiologies. Prematurity, intrauterine hypoxia, perinatal infections, and maternal complications account for 60 to 80% of perinatal losses.

Maximizing the health and well-being of the mother and fetus by appropriate medical intervention is the general goal of obstetrical care. Effective monitoring of a fetus may require continuous assessment, and is commonly performed using electronic technology. However, recent escalation of the frequency of normal births by cesarean section has called into question the validity of present monitoring techniques with respect to specificity of identifying the fetus at risk. Reducing the number of unnescessary cesarean sections and, in general, reducing the number of babies that are seriously ill at birth has been raised as a national health care priority in an effort to reduce the cost of both short- and long-term health care.

Fetal assessment in this context is intended to detect conditions that, if continued; would likely result in fetal and newborn damage or death. The condition of the fetus is reflected by the cardiovascular responses in utero and may be recognized by monitoring the fetal heart rate.

The difficulties in monitoring fetal well-being have long been recognized by the medical profession. The variable position of the fetus within the womb, surrounded by the amnion and amniotic fluids makes direct examination of the fetus impossible or very difficult using most examination techniques.

Present electronic fetal heart rate monitoring shows great sensitivity, but inadequate specificity, and poor positive predictive value in correlating fetal heart rate changes with subsequent adverse neonatal outcome. Such electronic fetal heart rate monitoring, despite these limitations, remains an integral part and standard of care in the assessment of fetal status.

Presently, the primary non-invasive fetal monitoring technique is the Doppler/tocometer. The technique is cumbersome and subject to data loss as a result of fetal and maternal movement. Typically, a Doppler transducer is placed on the mother's abdomen in a position that focuses the ultrasound signal at the fetal heart. Should the fetus move relative to the transducer, it is highly likely that the transducer will no longer be in proper position and, thus, not record an accurate heart signal. In fact, the use of a Doppler monitor is not precise enough for reliable analysis of subtle heart rate changes.

U.S. Pat. No. 5,257,627 to Rapoport relates to a portable apparatus for the non-invasive, simultaneous, self-testing of fetal and maternal signals. The device has a signal processing means for simultaneously processing fetal heart rate and maternal input signals, and also has a communication linking means for the simultaneous transmission of the fetal heart rate and maternal input data to a remote output device. Rapoport's device uses ultrasonic means to detect the fetal heart rate.

Other non-invasive techniques are also in use. These include the processing of electrocardiograph and electromyogram signals for determination of the fetus's well-being.

U.S. Pat. No. 4,299,234 to Epstein et al. relates to a fetal heart rate monitor which combines electrocardiograph and electromyogram type signals to increase reliability and accuracy of the resulting heart rate information.

U.S. Pat. No. 4,781,200 to Baker relates to a self-contained, lightweight ambulatory fetal monitoring system for substantially continuous analysis of fetal well-being. The monitor includes a sensor garment which is worn by the mother and has a plurality of sensors. The sensors detect fetal heartbeats and movements of the fetus within the mother. Signals developed by the sensors are processed by signal processing equipment and analyzed by a programmable data processing unit which can be provided with a variety of analytical programs which are proposed to automatically and continuously analyze fetal well-being. The sensor belt goes around the waist of the mother, and thus obstructs the surgical field.

U.S. Pat. No. 5,042,499 to Frank et al. relates to a fetal heart rate monitor that monitors weak fetal electrocardiogram signals in the presence of strong interfering noise. Frank et al's invention non-invasively obtains from the abdomen of a pregnant subject the fetal $EKG_f$ signal, fetal heart rate, and accurate beat-to-beat heart rate variability. An operator views the $EKG_f$ signal and optimally places the set of thoracic electrodes in an attempt to adaptively cancel the maternal $EKG_f$ signal from the signal separately derived from a variably located abdominal electrocardiograph lead. There is no uniform placement of the abdominal electrodes for all patients. Placement of such leads is dependent on prior examination by a trained medical professional to identify optimal lead orientation.

The above patents, and all patents and publications mentioned in this application, are all incorporated herein in their entireties by reference.

Evaluation of the fetal electrocardiographic waveform itself might provide increased insight into the status of the fetus. Unfortunately, direct accessibility of the fetus has limited the electrocardiogram as an indicator of well-being. During labor, after the rupture of the amniotic sac, a fetal scalp electrode may be attached to the fetus's skin. This requires twisting a wire corkscrew electrode into the presenting part of the fetus, e.g., scalp or buttocks, via the vaginal opening.

In the absence of direct electrode contact with the fetus, a large maternal signal and the presence of electrical noise (e.g. muscle artifact) has substantially precluded recognition of the fetal electrocardiogram. The placement of a fetal scalp electrode is clearly invasive, generally less comfortable for the mother, and has associated increased risks, such as infection, to the fetus, mother, and caretakers. The issue of infection has received more attention recently with increased risks of serious bloodborne infections such as AIDS.

Regardless of the monitoring technique, critical difficulties frequently arise when there is an emergent need to transfer the monitored patient from the labor area to the operating room. The monitors are usually detached during this critical interval with the mother and her fetus unmonitored during the transfer. Reattachment to monitors in the operating room (if at all) requires additional, possibly precious time and attention. Doppler transducers, if used, are inevitably in the operative field for an emergency cesarean section. Likewise, scalp electrodes must be removed or cut and withdrawn with the baby through the abdominal incision, again increasing the risk of infection.

This established need, therefore, creates a requirement for a reliable, accurate, and noninvasive technique to monitor the electrocardiogram of the fetus. Furthermore, the technique must maintain a clear operative field, accommodate movement of the mother and fetus, and be usable for a relevant portion of gestation. Moreover, it will be very desirable for the monitor output to include the fetal electrocardiogram waveform in addition to the fetal heart rate and description of heart rate variability. Monitoring of maternal heart rate and the state of uterine contractions and noise artifacts attributable to the uterus would also be desirable.

SUMMARY OF THE INVENTION

The present invention provides a method of monitoring a fetal biopotential waveform. More particularly, the present invention provides a method for generating a fetal biopotential waveform and using the waveform components to monitor many variables including, but not limited to, the fetal heart rate, the fetal heart rate variability, and/or the fetal heart vector orientation of a fetus in a pregnant mother. The method includes the steps of measuring at least one biopotential waveform indicative of the mother's heart beat to form a maternal waveform, measuring at least one biopotential waveform indicative of the combined maternal and fetal heart beats to form a combined biopotential waveform, and using signal processing to cancel the maternal waveform from the combined waveform to derive a fetal waveform indicative of the fetus's biopotential electrocardiographic waveform ($EKG_f$).

The present invention also provides an apparatus for monitoring a fetal biopotential waveform. The present invention also provides an apparatus for generating a fetal biopotential waveform and using the waveform to monitor the fetal heart rate, the fetal heart rate variability, and/or the fetal heart vector orientation of a fetus in a pregnant mother. The apparatus includes at least one sensor, e.g., an electrode, for measuring at least one biopotential waveform indicative of a maternal heart beat, at least one sensor for measuring at least one biopotential waveform indicative of the combined maternal and fetal heart beats taken from a pregnant mother, and signal processing hardware, software, or hybrid mixes that can cancel the maternal waveform from the combined waveform to form a waveform indicative of the $EKG_f$.

The present invention non-invasively and passively measures fetal and maternal electrocardiographic and maternal electromyographic waveforms by using traditional surface electrode electrocardiographic and electromyographic techniques combined with adaptive signal processing methods to solve the problems associated with the devices/techniques described above. The invention provides patient information (e.g., fetal heart rate/variability, taking into account noise artifacts attributable to uterine contractions) that at least duplicates current clinical standards.

In particular, the invention uses, for example, suitable skin contact electrodes connected to amplifiers to acquire biopotential waveforms and form signals, preferably differential signals, indicative of the mother's heart beat from sensors, e.g., electrodes, placed on her chest, and indicative of the combined maternal and fetal heart beats from sensors placed on the mother's abdomen, lower back, or both, as well as electromyographic signatures indicative of noise artifacts attributable to changes in uterine tone. Maternal heart rate, heart rate variability, and respiration rate are derived from the chest signals; standard maternal EKG is derived from planar leads. Instead of differential signals, more vectors may be formed by collecting single-ended signals and creating "differential pairs" therefrom.

The sensors placed on the mother's abdomen, lower back, or both, are preferably placed to form pairs of sensors wherein each sensor of the pair is spaced from the other and each pair is positioned in a substantially criss-crossed pattern with respect to other sensor pairs. Substantial spacing between the sensors of each sensor pair and between pairs of sensors is preferred so as to achieve a three-dimensional processing of the fetal biopotential waveform. As mentioned above, the sensors are preferably positioned to avoid blocking any surgical fields, for example, the abdominal area. By sensing the combined fetal and maternal waveforms with a multiplicity of sensors, the uniqueness of the vectors can be used to establish the vector orientation of the fetus. Preferably, the number of vectors used is sufficient to achieve a clear signal indicative of the combined fetal and maternal waveforms. If a clear enough combined signal is obtained from a single sensor, the present invention can operate using a single sensor to obtain the combined waveform.

The signals from the abdominal electrodes are divided into a plurality of channels. After data validation, an adaptive signal processing filter (ASPF) algorithm or other suitable algorithm is used to cancel the estimated maternal waveform from each channel in the abdominal electrodes, using chest signals as references. The system then selects from at least one of the resulting waveforms to serve as the reference fetal waveform, for example, the waveform with the highest peak-to-peak amplitude. Using another ASPF or other suitable algorithm, the reference waveform is then processed against the other abdominal waveforms with the maternal waveforms canceled to form an enhanced fetal signal that is a representation of the $EKG_f$. The $EKG_f$ can subsequently be used to measure fetal heart rate and other biophysical profile parameters. Surface electromyogram (EMG) signals allow for concurrent monitoring of uterine contractions and afford improved cancellation of motion artifacts including noise attributable to skeletal muscles and uterine contractions.

The present invention provides a device that is totally non-invasive, passive and will supplant the fetal scalp electrode and, therefore, eliminate those risks of infection. In one embodiment, all signals are derived from standard EKG electrodes applied to the patient's skin.

The present invention also provides a device with sensor placement, e.g., probe electrode placement, that is universal across the patient population. Furthermore, in embodiments of the present invention wherein sensor strips or other free floating sensors, e.g., non-adhesive, are used to contact the mother's chest, abdomen, and/or back, the patient's position can be rotated or reorientated relative to the sensor field. In such an embodiment, the sensors must be capable of sensing a respective waveform without the need to be adhered to the patient's body.

The present invention also provides a device where the placement of the electrodes maintains a clear surgical field, thereby facilitating operative procedures such as cesarean section deliveries, and will not interfere with resuscitation of the mother, should either become necessary.

The present invention also provides a device that overcomes the signal loss anomaly of ultrasound devices resulting from fetal movement. There is no need to tend to the device and reposition electrodes as the fetus moves, thereby allowing health professional time and attention to be directed toward more productive patient care activities.

The present invention also provides a device that will achieve a full representation of the fetal $EKG_f$ waveform which may provide useful information about the fetal condition.

The present invention also provides a device which upon interpretation of the fetal $EKG_f$ waveform makes the subject device capable of determining the instantaneous orientation of the fetal heart vector, thereby indicating the orientation of the fetus and permitting prediction of delivery complications associated with atypical presentation.

The present invention also provides a device that routinely collects maternal EKG signals. Thus, collateral information about the well-being of the mother and possible maternal-fetal interactions are immediately available.

The present invention also provides a device that will function for an ambulatory patient, either pre-term or during prolonged labors where the patient wishes to ambulate.

The present invention also provides a device that can be used in the case of non-imminent deliveries, for example, pre-term patients who may have high risk pregnancies.

The present invention also provides a device that computes and displays a unique monitoring reading that provides a measure of the instantaneous processing performance.

The present invention also provides a device that computes and displays heart rate variability information in at least two forms: i) long term variability trend, as is available with current commercial systems; and ii) a unique measure of instantaneous variability.

The present invention also provides a means to monitor multiple gestations with no additional sensors and/or processing techniques being required.

The present invention also provides a device that routinely collects electromyographic (EMG) signals as a means for monitoring maternal uterine contractions and for providing an additional signal input for noise cancellation. In addition, the device also permits the identification and characterization of active (maternal movement) and passive (surgical manipulation, uterine contraction) maternal signals from EMG inputs useful for canceling noise artifacts to even further enhance the $EKG_f$.

The accompanying drawings, which are incorporated in and constitute a part of this application, illustrate several embodiments of the present invention and together with the description serve to explain the principles of the present invention.

DETAILED DESCRIPTION OF THE PRESENT INVENTION

Figure 1:
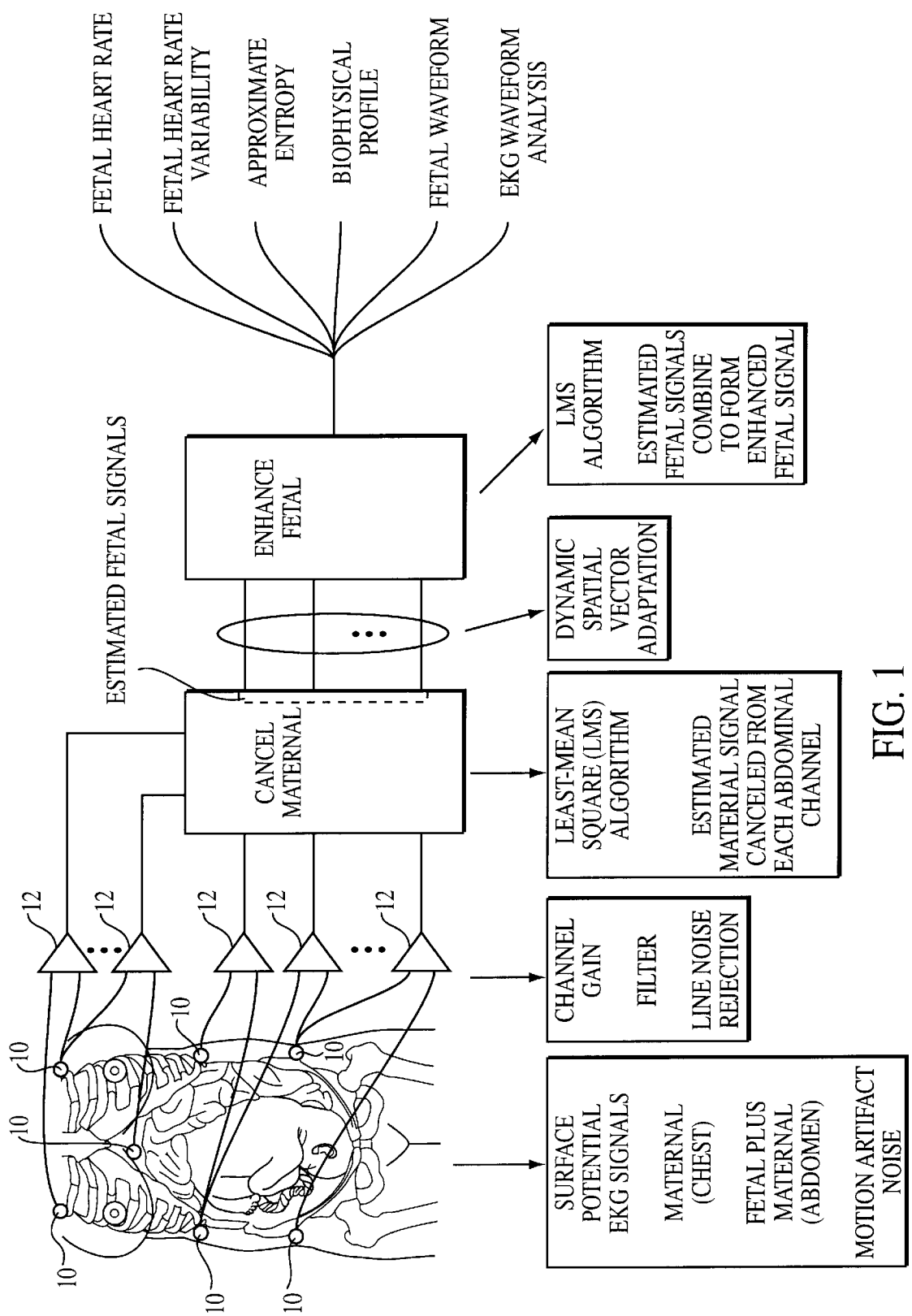
FIG. 1 is a block diagram of the preferred concept of the present invention.

The present invention provides a method of monitoring a fetal biopotential waveform. More particularly, the present invention provides a method for generating a fetal biopotential waveform and using the waveform to monitor the fetal heart rate, the fetal heart rate variability, and/or the fetal heart vector orientation of a fetus in a pregnant mother. The method includes the steps of measuring at least one biopotential waveform indicative of the mother's heart rate to form a maternal waveform, measuring at least one biopotential waveform indicative of the combined maternal and fetal heart rates to form a combined biopotential waveform, and using signal processing to cancel the maternal waveform from the combined waveform to derive a fetal waveform indicative of the fetal electrocardiographic waveform ($EKG_f$).

The present invention also provides an apparatus for monitoring a fetal biopotential waveform and an apparatus for monitoring the fetal heart rate, the fetal heart rate variability, and/or the fetal heart vector orientation of a fetus in a pregnant mother. The apparatus includes at least one electrode for measuring at least one biopotential waveform indicative of a maternal heart rate, at least one electrode for measuring at least one biopotential waveform indicative of the combined maternal and fetal biopotential waveform taken from a pregnant mother, and a signal processing circuit that can cancel the maternal waveform from the combined waveform to form a waveform indicative of the fetal electrocardiographic waveform ($EKG_f$).

According to a preferred method of the present invention, the maternal biopotential waveform is preferably acquired from at least one sensor, e.g., a skin contact electrode, and preferably from two or more sensors, placed on or in contact with the mother's chest, upper back, or both. The combined waveform is acquired from at least one sensor, e.g., a skin contact electrode, and preferably from two or more sensors, placed on or in contact with the mother's abdomen and/or lower back. Preferably, the combined waveform is acquired by combining the signal from at least one sensor placed on or in contact with the mother's abdomen and at least one other sensor placed on or in contact with the mother's abdomen, lower back, or both. Other devices to acquire the signals or waveforms mentioned throughout can be used and include sensors that may be mounted on a table or chair that the mother rests on, or non-contact sensors such as magnetometers and the like that can be spaced from the surface of the mother's skin.

The combined waveform can be preferably derived, according to the invention, from a plurality of signals acquired from a plurality of sensors placed on the mother's abdomen, and by dividing the signals into a plurality of channels. The method then includes canceling an acquired maternal waveform from each channel to form a plurality of resulting waveforms, and selecting at least one of the resulting waveforms as a reference fetal waveform. The selected waveform can be, for example, the waveform with the highest peak-to-peak amplitude. The selected reference fetal waveform is enhanced using an adaptive signal processing filter algorithm or another suitable algorithm to remove correlated noise by processing against the remaining resulting waveforms that were not selected as the reference fetal waveform. The signal strength of the various resulting waveforms can then be compared and the detected signal characteristics of the resulting waveforms can be used to infer a heart vector orientation and the position of the fetus. The signal processing algorithm can use a least mean squares (LMS) algorithm to dynamically weigh all of the waveforms derived from the sensor on the mother's chest against each of the waveforms derived from each of the sensors on the mother's abdomen and/or lower back. An exemplary teaching of an LMS filter algorithm that can be used in the methods and apparatus of the present invention is described in U.S. Pat. No. 5,891,045, and the references cited therein, including Changxiu et al., "A New Algorithm for Adaptive Noise Cancellation Using Singular Value Decomposition," *Acta Automatica Sinica*, Vol. 12, No. 2, pp. 146–153 (April 1986); Damen et al., "The Use of the Singular Valve Decomposition in Electrocardiology," *Medical & Biological Engineering & Computing*, pp. 473–482 (1982); and Widrow, "Adaptive Interference Canceling," *Adaptive Signal Processing, Applications Part IV*, Chap. 12, Prentice-Hall, Englewood Cliffs, N.J., pp. 302–367 (1985), which are all incorporated in their entireties herein by reference.

The fetal electrocardiographic waveform derived according to the method and apparatus of the present invention can be visually analyzed by observing a visual display of the waveform or by inspecting other forms of data acquired that correlate with or have a relationship to the waveform. A trained technician can visually analyze the waveform to determine any abnormalities in the visual representation of the waveform and thus can determine any abnormalities in the fetus' well-being. Over time, a table or library of normal $EKG_f$'s can be obtained so that technicians can become familiar with normal fetal electrocardiographic waveforms and be able to determine abnormalities in subsequently tested fetuses. Trained technicians can, at a glance, by visually inspecting the displayed electrocardiographic waveform, make a determination of a fetus' well-being (normality of $EKG_f$) in a reliable and non-invasive manner.

According to advantageous embodiments of the present invention, the sensors placed on the mother's abdomen and/or lower back are preferably spaced away from the lower anterior abdomen or, for example, away from the lower right-side anterior abdomen so as not to interfere with a cesarean section delivery of the fetus, an appendectomy operation or other procedure should such procedures be necessary. The skin sensors placed on the mother's chest are preferably placed, for example, away from the midline of the chest so as not to interfere with resuscitation attempts on the mother, should such attempts be necessary.

The sensors used to transduce the biopotential signals of interest may preferably be skin contact electrodes. Exemplary electrodes include silver-silver chloride (Ag—Ag Cl) dot electrodes that make contact with the skin on one or more sides and are in contact with an electrical contact (e.g., a snap) on the other side. The skin is generally prepared in order to provide a good electrical interface with the dot electrode. For instance, the skin may be wiped with alcohol, subject to slight abrasion, and coated with an electrode gel. After the preparation, the dot electrode is applied and wired into an amplifier of the signal processing system. Good technique in skin preparation is helpful when the sensors employed are skin contact electrodes. Poor electrode interfaces can lead to excessive noise on the signal lead, potential for external pick-up, and similar problems. These "extra" noises or noise sources are likely to be of such a character that they may interfere with the extraction and enhancement of the fetal electrocardiographic waveform.

To eliminate bad signals, the present invention provides a method to automatically identify, assess, and validate the signal integrity of the electrode or sensor. Although an exemplary device that can be used to make such an assessment is an impedance meter such as the Prep-Check, available from General Devices, making an impedance measurement requires that an active measurement be made, for example, by imposing a small current on the circuit and measuring the voltage drop. Accordingly, the present inventors have developed a preferred method of using the passive amplifier data to make an assessment of signal quality.

The signal quality can be tested by a variety of means, including testing the frequency character. The frequency character (spectrum) of the EKG signal preferably has a large low frequency component followed by a roll-off with increasing frequency. According to the present invention, amplifiers are used that preferably have a 60 Hz notch filter for rejecting line noise artifacts. After the notch filter, the signal rises slightly to a flat noise floor. According to the present invention, "good" EKG signals preferably repeatedly and reliably exhibit this spectrum, whereas "bad" EKG signals do not exhibit a 60 Hz notch characteristic and reach a noise floor at a lower frequency and at a higher relative amplitude. These distinctions are used to validate whether a channel is good or bad. A segment of the EKG signal is preferably processed by an algorithm known as a fast fourier transfer (FFT) to generate the frequency spectrum. Then, a ratio of the signal energy at a low frequency (approximately 2 Hz) to the signal energy at 60 Hz (2 Hz energy/60 Hz energy) is measured. Good channels are those determined to have large ratio magnitudes whereas bad channels have smaller ratio magnitudes, depending upon the sensors used and the characteristics of the various signals that are obtained. Those channels that do not exceed a minimum ratio magnitude are deemed to be bad and are not used for subsequent processing. The ability to selectively include only "good" signals provides the apparatus with a high level of adaptability and robustness.

Signal processing and noise filtering/rejecting devices and components for such devices that are suitable for the methods and apparatus of the present invention include those components described in U.S. Pat. Nos. 5,853,364; 5,983,127; and 5,999,845, which are herein incorporated in their entireties by reference.

In yet other embodiments of the present invention, a device in accordance with the invention can be used off-site to monitor a pregnant women while going about her normal daily activities. The device can also include, for example, a thermometer or a motion sensor. Suitable motion sensors that can be used include, for example, accelerometers or inclinometers. These added devices can be included to provide an indication of the patient's condition at the time that certain changes in electrocardiographic waveform occur. The information acquired by the monitor might be stored and forwarded or might be used to identify problem situations. According to such an embodiment, collateral measurements of the activities occurring at the time a "suspect" event occurs may shed light on the nature of the event. For instance, if an episode of low fetal heart rate is identified, it would be helpful to a proper analysis of the low heart rate to know whether the mother was lying down or jogging. A possible motion sensor is described in U.S. Pat. No. 5,999,661, which is herein incorporated in its entirety by reference.

The apparatus of the present invention is described in more detail below and includes electrodes and signal processing circuitry to carry out the methods and complete the apparatus described above.

The preferred invention is shown in functional form in FIG. 1. The periodic beating of the human heart is induced by a biopotential waveform. In one embodiment, the waveform can be measured non-invasively by suitable skin contact electrodes 10 connected to differential amplifiers 12. The biopotential waveform of an electrically beating fetal heart, though small in proportion to its mother, will exist in combination with the maternal waveform.

Figure 2:
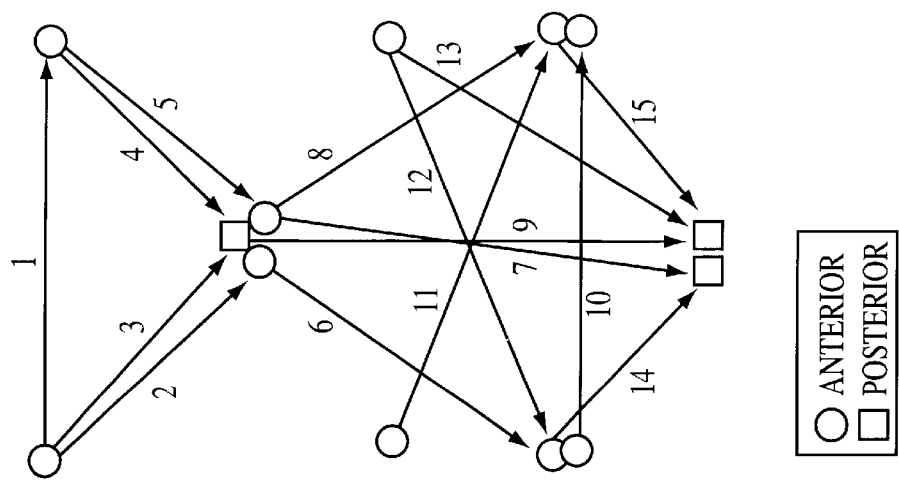
FIG. 2 illustrates exemplary electrode positions and signal channels for the present invention.
Figure 2:
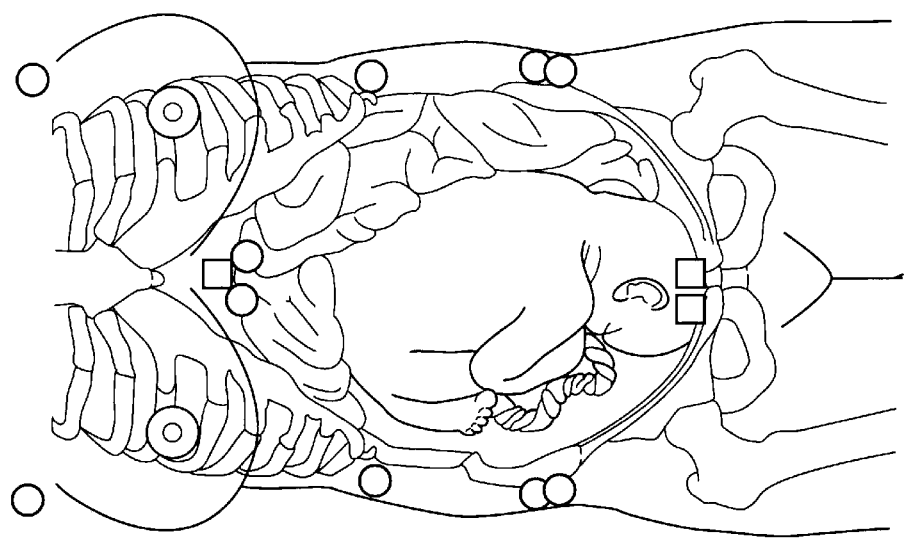

The invention preferably starts by acquiring maternal and maternal-plus-fetal biopotential waveforms. The maternal waveforms can be collected by surface electrodes preferably placed on the mother's chest and/or upper back, preferably on both sides, but not in the middle, of the mother's chest. By "upper back" what is meant is the portion of the back not below the level corresponding to the sternum. The maternal-plus-fetal waveforms or "combined waveforms" are collected by surface electrodes placed on the mother's abdomen and/or lower back, preferably on the sides of the mother's abdomen. By "lower back" what is meant is that portion of the back below the sternum. An exemplary electrode placement scheme is shown in FIG. 2.

A clinically significant aspect of the present invention is that the sensors (electrodes) are placed in an adaptable pattern, in other words, in a pattern irrespective of the fetal position, the maternal condition, or the size and shape of the mother. According to an advantageous embodiment of the present invention, the electrodes are preferably positioned in a manner so as to remain clear of usual potential operative sites. Equally significant is the fact that the successful implementation of the monitor is insensitive to variations in the placement of the electrodes; thus, a patient who is monitored at different points in time need not have the electrodes placed in the same exact location for each monitoring episode. The electrodes can be a plurality of separate electrodes or a small number, for example, two, of electrode strips. Each strip can contain a plurality of electrodes and preferably only a single cable assembly. According to a preferred embodiment of the present invention, two electrode strips are used and each strip contains a plurality of electrodes. Placement of the electrode strips can be routine, simple, and rapid.

Figure 3:
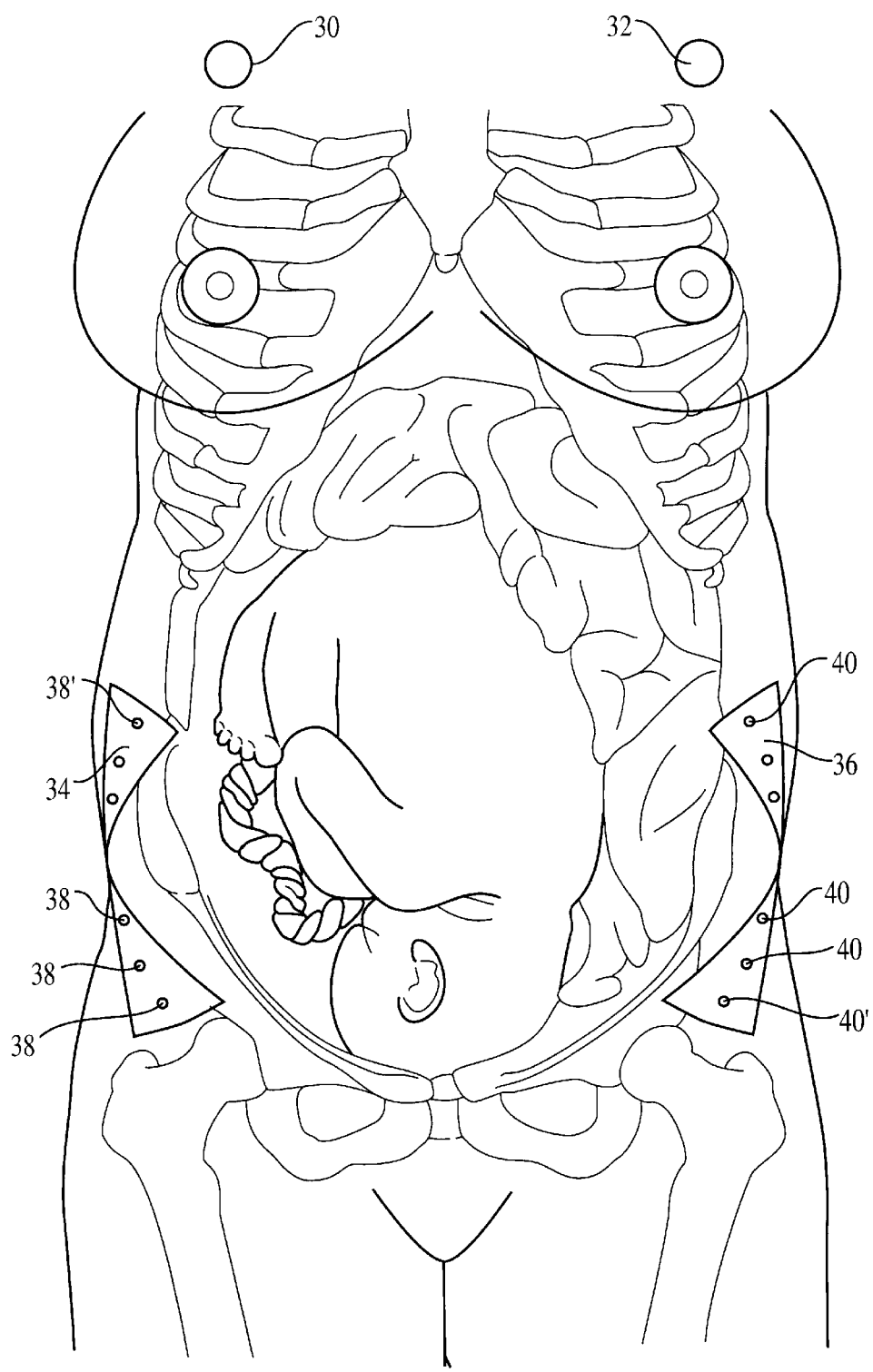
FIG. 3 is an illustration of a sensor placement scheme showing strip sensors positioned on opposing sides of a pregnant mother's abdomen in accordance with an embodiment of the present invention.

FIG. 3 is an illustration of a sensor placement scheme useful in accordance with the present invention. Chest sensors for monitoring the maternal biophysical waveform are shown in the form of skin contact electrodes 30, 32. The abdominal sensors for acquiring the combined fetal and maternal biophysical waveform are shown in the form of strip sensors 34 and 36. As can be seen in FIG. 3, strip sensor 34 includes a plurality (seven in the strip sensor shown) of individual sensors 38 along the length of the strip sensor 34. Likewise, strip sensor 36 includes a plurality of sensors 40 (seven in the strip sensor shown) spaced along the length of strip sensor 36.

Figure 4A:
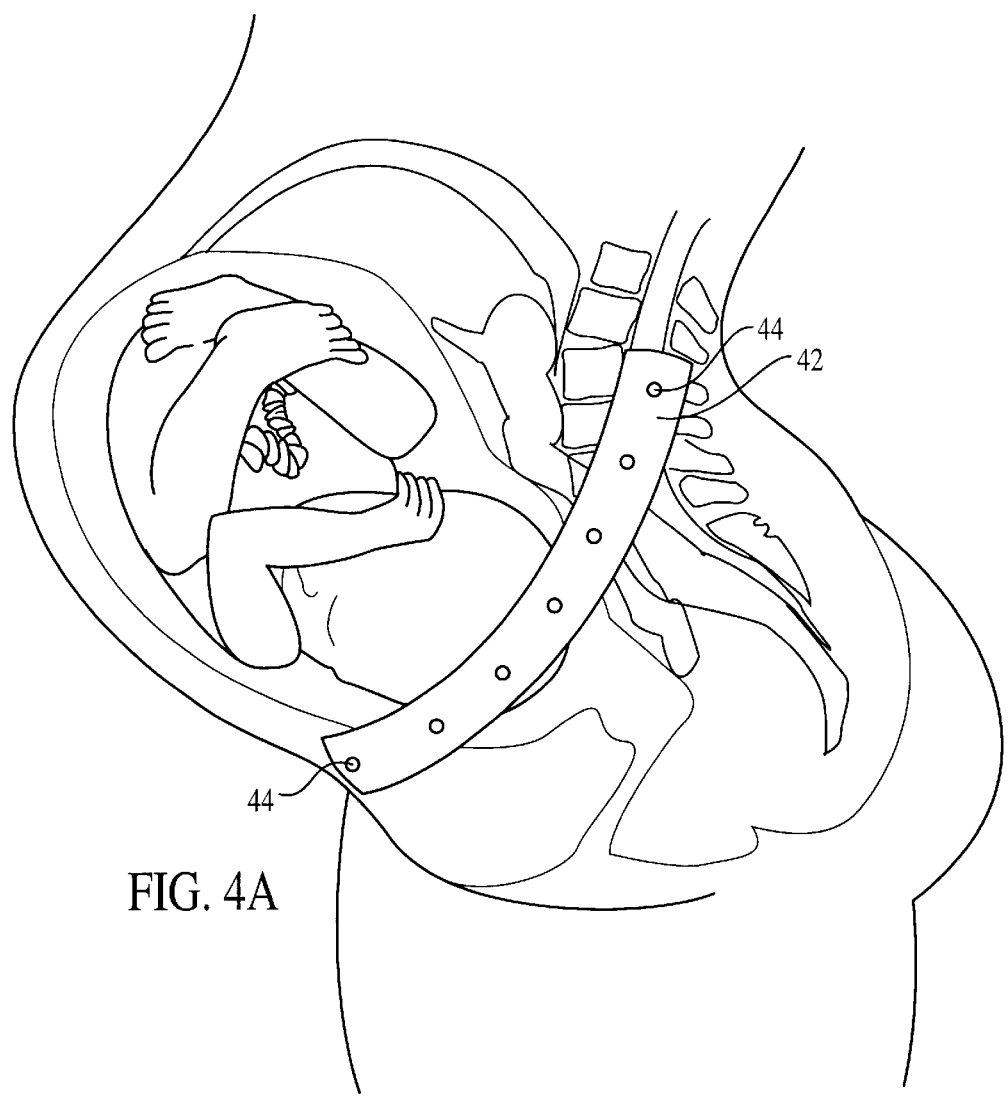
FIG. 4 is an illustration of a sensor placement scheme showing a strip sensor in place and a strip sensor connected to an electrode interface.
Figure 4B:
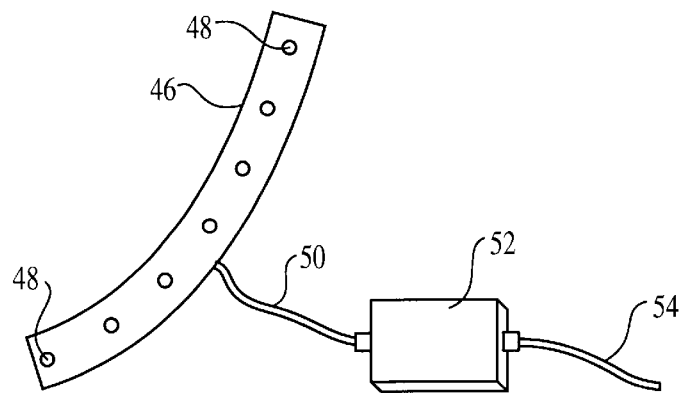

FIG. 4 shows the operative positioning of a left-side strip sensor 42 containing seven sensors 44 spaced along the length of strip sensor 42. The strip sensor 42 is positioned in the same place as the left-side sensor shown in FIG. 3. As shown in FIG. 4, the strip sensor is positioned on the pregnant mother along the lower anterior abdomen away from the operative field necessary for a cesarean section delivery, and wrapping around the curve of the mothers lower abdomen. Also shown in FIG. 4 is a strip sensor 46 containing seven individual sensors 48 spaced along the length of strip sensor 46. Strip sensor 46 is not in an operative position but is shown to demonstrate that a singular lead 50 carrying signals from each of the seven individual sensors 48 can be employed and can be interfaced with an electrode interface 52 from which a lead 54 extends to carry the signals for further signal processing.

According to the present invention, numbers of differently oriented vectors are collected for both signal types (maternal only and maternal-plus-fetal). Pairs of electrodes (channels) are assigned to individual differential amplifiers. An exemplary channel would include the pair of electrodes 38', 40' shown in FIG. 3. All channels are preferably amplified and filtered in order to reject noise and provide anti-aliasing for subsequent digitization. In one embodiment, all channels are sampled at a rate less than or equal to 250 samples/second. When sampling involves digitization, a resolution of less than or equal to 16 bits is preferred. Other sampling methods can be used, including analog methods, hybrid analog/digital methods, or combinations of sampling methods. Channel validation as discussed above is preferably used to assure that non-informative or corrupt ("bad") chest channels are excluded from the processing.

The first phase of signal processing applies an Adaptive Signal Processing Filter (ASPF) algorithm to cancel the estimated maternal (chest) waveform from each abdominal channel. The result is a set of estimated fetal signals plus residual noise. Maternal heart rate, heart rate variability, and respiration rate are derived from chest signals. A standard maternal EKG can be derived from planar leads.

Figure 5:
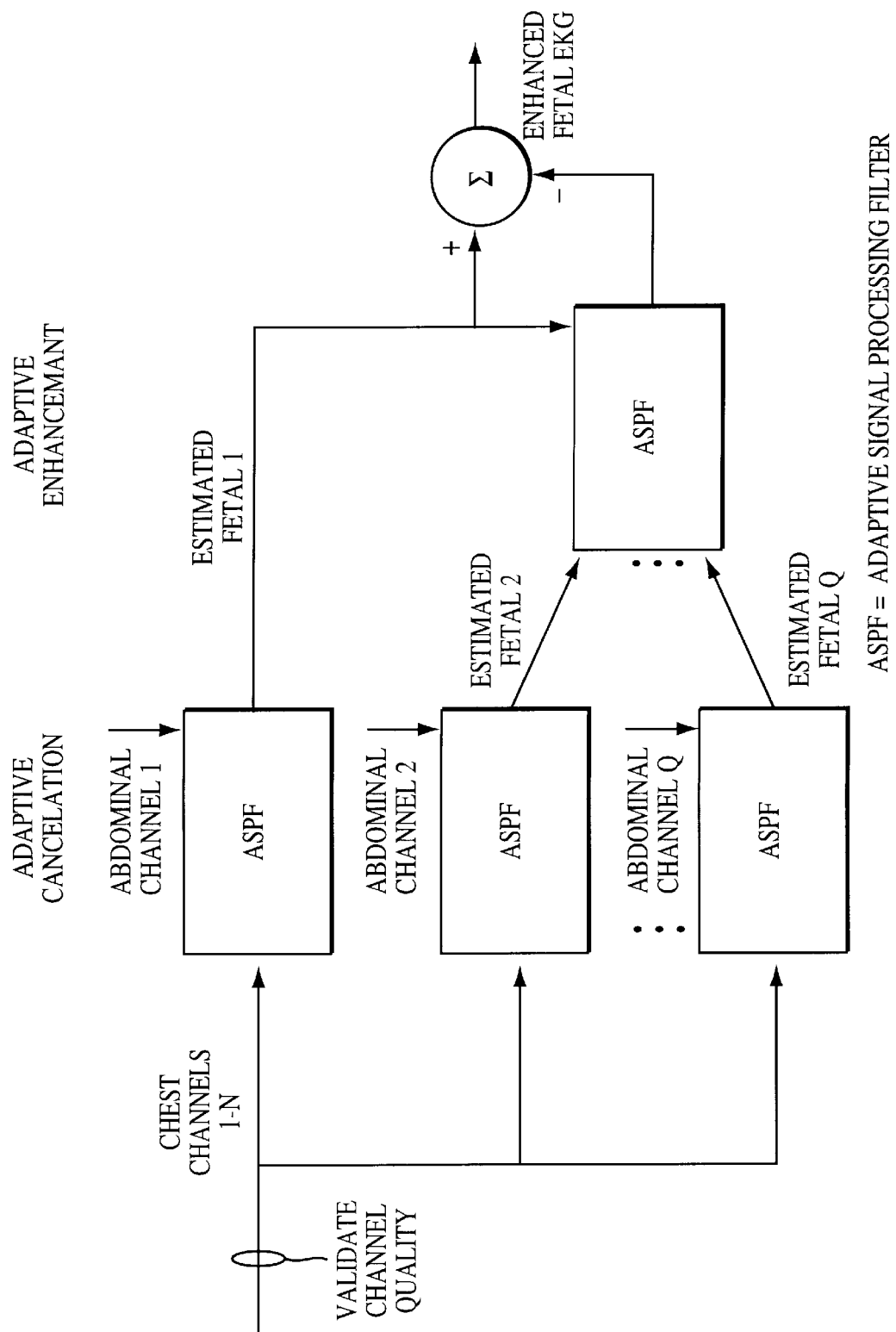
FIG. 5 is a functional block diagram of the signal processing of the invention.
Figure 6:
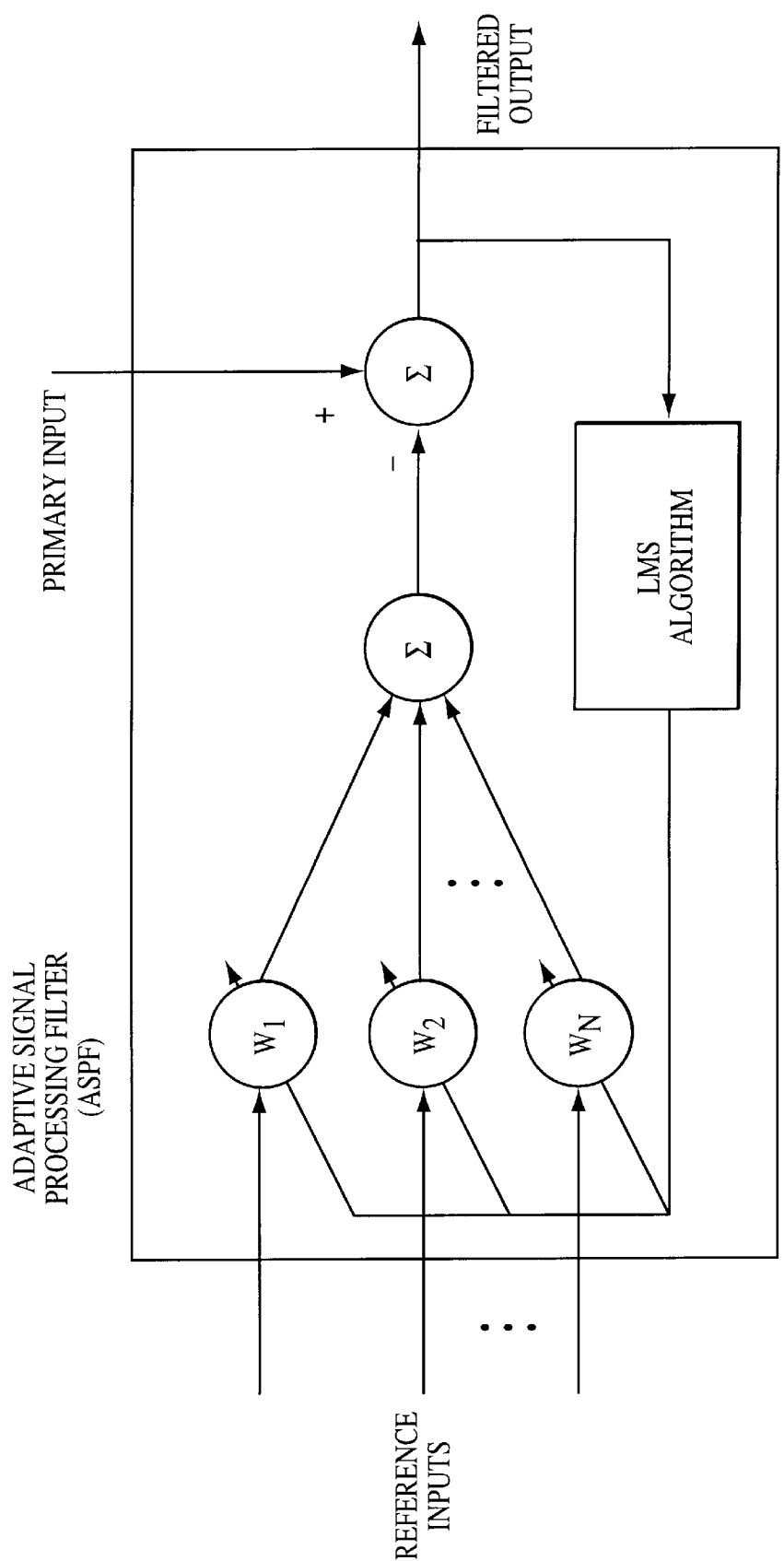
FIG. 6 illustrates an exemplary adaptive signal processing filter (ASPF) used in the invention's signal processing, the ASPF using a Least-Mean-Squares (LMS) algorithm.

The implementation of the ASPF algorithm is shown functionally in FIG. 5 (for the overall configuration) and in FIG. 6 (for each individual filter). All chest channels are dynamically weighted against individual abdominal channels in order to effect the cancellation of the estimated maternal (chest) waveform from each abdominal channel. Several bipolar leads measure the electrical signal (reference) across the maternal chest (Chest Channel 1 . . . N). Several additional bipolar leads measure the signal from the maternal abdomen (Abdominal Channel 1. . . Q). The chest leads are used as a basis to cancel the maternal signal from the abdominal leads (Estimated Fetal 1 . . . K). The abdominal leads are enhanced to derive the resulting fetal EKG$_f$. Additional reference signals (e.g., EMG) can be included to optimize noise cancellation. All components used to implement the algorithms are commercially available individually. A filter chip co-processor as described in U.S. Pat. No. 5,931,892, which is incorporated herein in its entirety by reference, can be used, for example, to implement the ASPF algorithm.

Preferably, the resultant estimated fetal waveforms will exhibit a range of peak-to-peak amplitudes as a consequence of the orientation of the fetal heart relative to the abdominal vector orientations. At least one of the resultant waveforms is selected as the reference for the next phase of processing, for example, the waveform with the largest peak-to-peak amplitude. Channel validation can preferably be used to assure that non-functional or corrupt abdominal channels are excluded from the processing.

The selected reference fetal waveform happens to be Estimated Fetal 1 in FIG. 5 although any of the estimated fetal signals can be selected. One method of selecting the estimated fetal signal is to choose the signal with the largest peak-to-peak amplitude. Using the same ASPF algorithm of FIG. 5, the selected estimated fetal signal is enhanced to remove correlated noise, by processing against the remaining abdominal estimated fetal waveforms. The enhanced fetal signal that is the output of this step is a representation of the fetus's biopotential electrocardiogram (EKG$_f$) and can be used to assess or monitor fetal conditions including the well-being of the fetus. The EKG$_f$ can be used to assess fetal well-being by measuring fetal heart rate, fetal heart rate variability, and approximate entropy, as well as defining orientation of the fetus within the mother, and/or other components of biophysical profile parameters. Fetal heart rate and heart rate variability are derived, preferably through R-to-R interval timing, or by appropriate auto-correlation processing of either the enhanced fetal signal or one or more of the processed abdominal signals. Fetal position, inferred from the heart vector orientation, is determined by the signal strength and polarity of the EKG$_f$ waveform relative to the abdominal electrode pairs. The maternal heart vector can be used as a reference point for determining the fetal heart vector. The three-dimensional nature of the abdominal array readily accommodates movement of the fetal heart vector without loss of signal. Because maternal EKG signatures are collected as an integral part of the process, similar biophysical profiles can be determined for the mother. Though not shown in FIG. 1, surface EMG signals allow for monitoring of uterine contractions and afford improved cancellation of motion artifacts.

Figure 7:
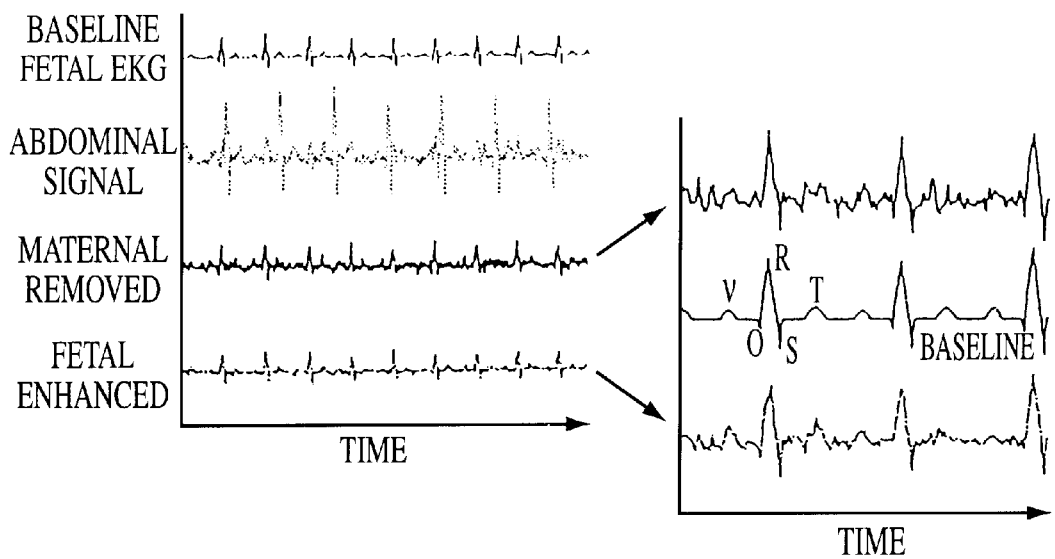
FIG. 7 illustrates results using the present invention with simulated data. Characteristic simulated fetal (Baseline Fetal) and maternal EKG signals were summed together (Abdominal) with noise in order to validate the signal processing algorithms. Fetal R-peaks are evident (Maternal Removed) following the first state of processing; significant noise reduction is evident (Fetal Enhanced) following a second stage of processing.
Figure 8:
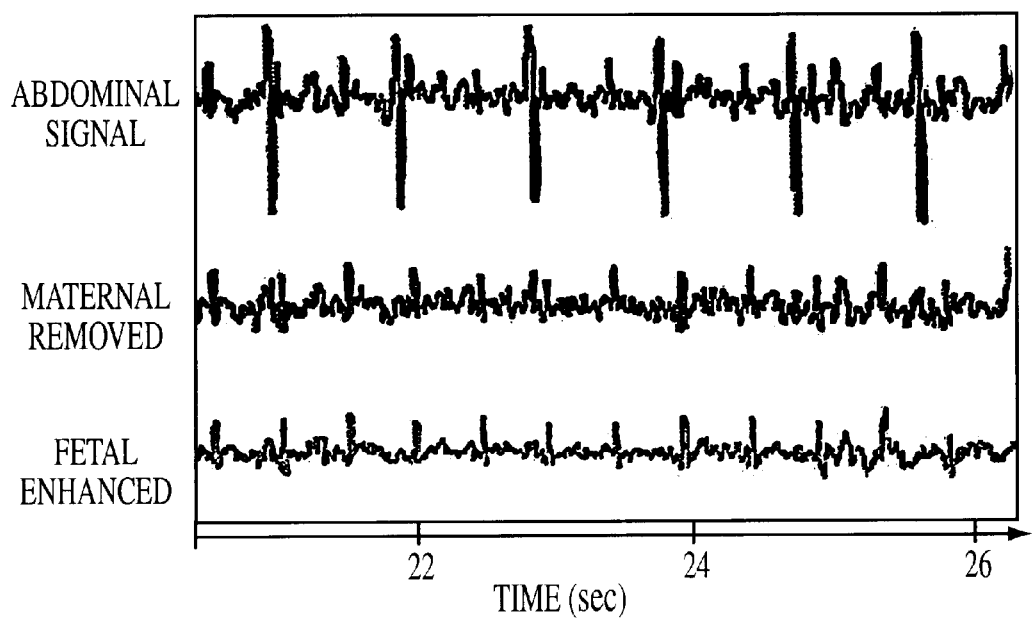
FIG. 8 illustrates results with representative clinical data. Data sample collected in the clinical environment using the present invention. The three signal traces correspond to the simulation data shown in the inset of FIG. 7. The jagged appearance of the signals is an artifact of graphics manipulation and not a system limitation.

The invention has been validated both with simulated data (FIG. 7) and human clinical data (FIG. 8). Analysis from 20 human subjects, collected as part of an approved research protocol, have been used to demonstrate reliable determination of fetal heart rate and fetal heart rate variability. The inclusion of an EMG as an additional reference signal can be used to more fully refine the EKG$_f$ waveform derivation and address noise artifacts that otherwise mask smaller waveform features while enhancing the system robustness in the face of skeletal and uterine muscle noise caused by maternal motor activity.

The monitor concept and algorithms can be validated using simulated data comprised of a representative fetal EKG$_f$ signal (FIG. 7). To this representative signal a maternal signal of an amplitude proportional to a standard signal reported in literature can be added. The fetal and maternal EKG's were randomly dithered in both amplitude and repetition rate. In addition, a baseline noise level, characterized by what is seen in the clinical situation, was also added to this composite. This signal was then processed by the algorithm to first adaptively cancel the maternal signal, and then adaptively enhance the resulting fetal signal to identify the underlying signal. The results from clinical data (FIG. 8) demonstrate comparable performance.

The present invention will be further clarified by the following examples, which are intended to be exemplary of the present invention.

EXAMPLES

Twenty subjects were monitored using a device according to the present invention. The device comprised a MP100 system (BIOPAC Systems, Inc.), with 16 ECG100B electrocardiogram amplifiers (BIOPAC Systems, Inc.), an Acq-Knowledge (BIOPAC Systems, Inc.) data acquisition application and MATLAB device and signal processing toolbox (MathWorks, Inc.), several Silvon Diaphoretic Electrodes (New Dimensions in Medicine (NDM)), and a MATLAB-based application code to implement the various algorithms. A small number of the subjects were simultaneously monitored with a Doppler. There was no interference between the system of the present invention and the Doppler ultrasound and the results qualitatively showed good correlation between fetal heart rate measurements. Nineteen of the 20 subjects were in the range of 28 to 36 weeks of gestation. The remaining subject was not pregnant, and she was monitored in order to establish a system noise baseline. Two of the subjects were twin gestations and discrimination between the heart signatures was effected.

All data collected used the universal electrode positions (avoiding potential surgical sites) as shown in FIG. 2, as opposed to fetal-specific positions as has been reported in U.S. Pat. No. 5,042,499 to Frank et al. User-attended batch processing was used to demonstrate feasibility. Inclusion of a uterine contraction measurement, automation of the dynamic processes, and implementation of a real-time output could have been implemented.

Figure 9:
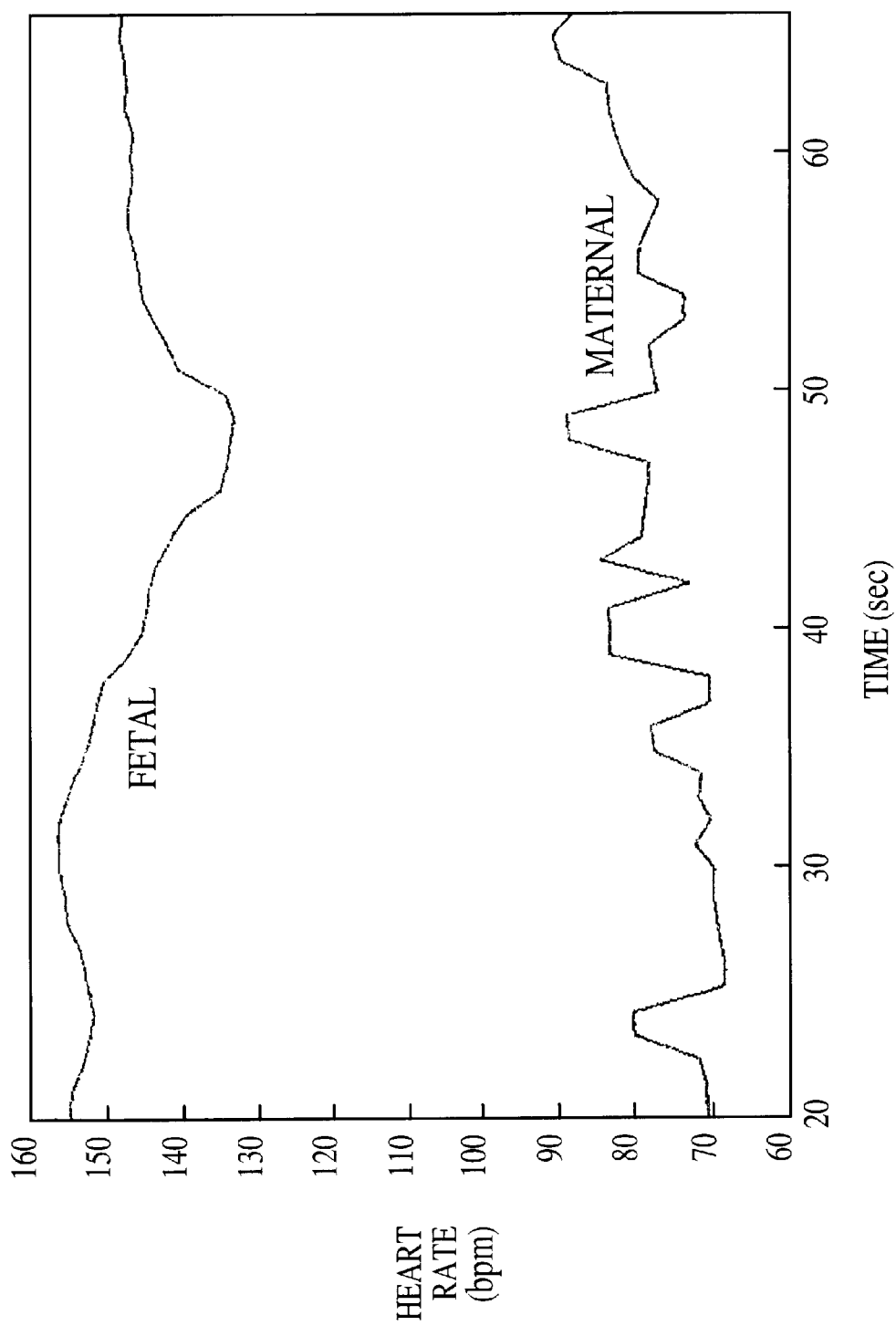
FIG. 9 is a graph showing the time histories of the fetal heart rate and the maternal heart rate derived from waveforms acquired according to the present invention.

FIG. 9 demonstrates a use of the present invention in monitoring the deceleration of a fetus' heart rate as, for example, accompanying uterine contractions. Both the fetal heart rate and the maternal heart rate shown in the graph of FIG. 9 were derived according to the method and apparatus of the present invention. FIG. 9 shows that during the time period of from about 48 to about 50 seconds there was a corresponding, and normal, deceleration of the fetal heart rate.

The present invention is a reliable, accurate, non-invasive, and passive technique to measure the electrocardiographic waveform of the fetus. Furthermore, the present invention maintains a clear operative field, accommodates movement of the mother and fetus, and is usable for a relevant portion of gestation. The monitor's output can include the fetal electrocardiographic waveform in addition to the fetal heart rate, and includes a description of heart rate variability as well as maternal heart rate and noise artifacts attributable to uterine contraction.

Other embodiments of the present invention will be apparent to those skilled in the art from consideration of the specification and practice of the present invention disclosed herein. It is intended that the specification and examples be considered as exemplary only, with a true scope and spirit of the invention being indicated by the following claims and equivalents thereof.

What is claimed is:

1. A method of monitoring the fetal electrocardiographic waveform of a fetus in a pregnant mother, said method comprising:

measuring at least one biopotential waveform indicative of the maternal heart beat, said maternal biopotential waveform being acquired from at least one sensor located external to the mother at or near the mother's chest, to form a maternal waveform;

measuring at least one biopotential waveform indicative of the combined maternal and fetal heart signals to form a combined biopotential waveform, said combined waveform comprising a plurality of signals from sensors located at or near the mother's abdomen, lower back, or both, said sensors being located external to the mother and irrespective of the fetal position and to avoid blocking a surgical field, and said method further comprising dividing said signals into a plurality of channels, canceling the maternal waveform from each channel to form a plurality of resulting waveforms, and selecting one of the resulting waveforms to indicate a reference fetal waveform; wherein the selected reference fetal waveform is enhanced using an adaptive signal processing filter to remove correlated noise by processing against the remaining resulting waveforms that were not selected as the reference fetal waveform.

2. The method of claim 1, further comprising comparing the signal strength of the various resulting waveforms and using the detected signal strengths of the resulting waveforms relative to the sensors located at or near the mother's abdomen, lower back, or both to infer a heart vector orientation and the position of said fetus.

3. The method of claim 1, wherein said adaptive signal processing filter uses a least mean squares algorithm to dynamically weigh all of said waveforms derived from the at least one sensor at or near the mother's chest against each of the waveforms derived from each of said sensors at or near the mother's abdomen, lower back, or both.

* * * * *

UNITED STATES PATENT AND TRADEMARK OFFICE
CERTIFICATE OF CORRECTION

PATENT NO. : 6,751,498 B1
DATED : June 15, 2004
INVENTOR(S) : Robert S. Greenberg et al.

It is certified that error appears in the above-identified patent and that said Letters Patent is hereby corrected as shown below:

<u>Title page,</u>
Item [75], Inventors, delete "Christion" and insert -- Cristion --

Signed and Sealed this

Thirty-first Day of August, 2004

JON W. DUDAS
*Director of the United States Patent and Trademark Office*